United States Patent [19]

Legendre et al.

[11] 4,367,738

[45] Jan. 11, 1983

[54] PRE-FILLED SYRINGE FOR ABUSABLE DRUGS

[75] Inventors: Robert Legendre, Piscataway; Steven Schlossberg, East Windsor, both of N.J.

[73] Assignee: Janssen Pharmaceutica Inc., New Brunswick, N.J.

[21] Appl. No.: 315,800

[22] Filed: Oct. 28, 1981

[51] Int. Cl.³ .............................................. A61M 5/00
[52] U.S. Cl. ............................. 128/218 PA; 128/234
[58] Field of Search ......... 128/218 R, 218 PA, 218 P, 128/218 C, 218 F, 215, 216, 234, 220, 272; 222/153, 386

[56] References Cited

U.S. PATENT DOCUMENTS

| 2,632,445 | 3/1953 | Kas, Sr. | 128/218 F |
| 3,110,310 | 11/1963 | Cislak | 128/218 C |
| 3,126,004 | 3/1964 | Sarnoff | 128/218 |
| 3,366,113 | 1/1963 | Hobbs | 128/272 |
| 3,667,657 | 6/1972 | Chiquiar-Arias | 222/541 |
| 3,890,971 | 6/1975 | Leeson et al. | 128/218 P |
| 3,934,586 | 1/1976 | Easton et al. | 128/218 C |
| 3,949,748 | 4/1976 | Malmin | 128/218 C |
| 3,951,146 | 4/1976 | Chiquiar-Arias | 128/218 |
| 3,998,224 | 12/1976 | Chiquiar-Arias | 128/218 |
| 4,121,588 | 10/1978 | Geiger | 128/218 |

Primary Examiner—John D. Yasko
Attorney, Agent, or Firm—Geoffrey G. Dellenbaugh

[57] ABSTRACT

A pre-filled syringe suitable for administration of abusable injectable drugs which prevents surreptitious injection of the drug and replacement by an adulterant to avoid detection of the abuse.

3 Claims, 3 Drawing Figures

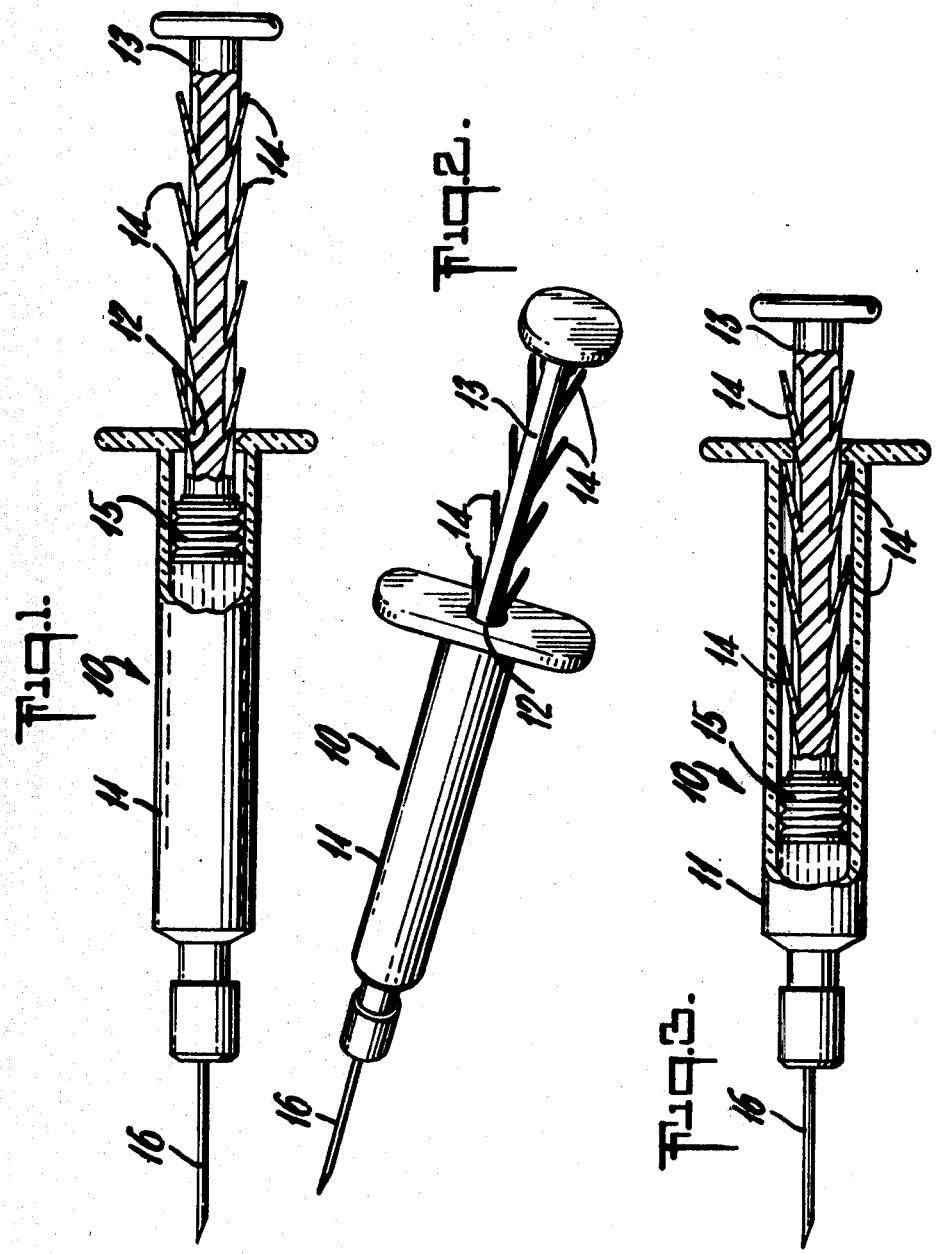

PRE-FILLED SYRINGE FOR ABUSABLE DRUGS

FIELD OF THE INVENTION

The present invention relates to syringes and more particularly to pre-filled syringes for abusable drugs which do not permit adulteration of the contained injectable formulation.

BACKGROUND OF THE INVENTION

The abuse of drugs is a problem of every increasing severity. Especially in hospitals and other medical facilities where abusable drugs such as narcotics are stored, this problem is of great concern to the medical community.

One aspect of this problem relates to the outright theft of narcotics by those only peripherally connected with the hospital. This problem can be prevented in large part by the strict security measures which are currently employed anywhere that abusable drugs are stored.

A more insidious aspect of this problem, however, is the surreptitious use of these drugs by medical personnel themselves. The proximity to and familiarity with abusable drugs can cause considerable temptation and lead to unfortunate results.

Such results can occur even more readily with pre-filled syringes then with the customary bottles and ampoules. For example, a pre-filled syringe of an abusable drug may be surreptitously used by a drug abuser and the syringe thereafter completely or partially filled with a foreign fluid (e.g., sterile saline). Aside from the evils which flow from drug abuse, this practice poses significant medical hazards for the patient since not only is the used syringe in an unsterile condition, but it also contains less active ingredient than it should. In a conventional syringe pre-filled with an abusable drug, there is no way of detecting the tampering and hence such conventional pre-filled syringes have generally not been used for abusable drugs.

Recognizing the problem with abuse of injectable drugs, several U.S. patents have addressed the problem by disclosing self-destructible syringes which render themselves unreusable. Examples of such U.S. patents are Geiger U.S. Pat. No. 4,121,588 and Chiquiar-Arias U.S. Pat. Nos. 3,667,657; 3,951,146; and 3,998,224. These syringes all share the property of either destroying themselves or being readily destroyable after use so that the syringes may not be reused for the injection of abusable drugs. These patents do not, however, address the problem of surreptitious injection of a portion of the substance contained in a pre-filled syringe, followed by the introduction of a foreign substance to disguise this use. In fact, these patents are not concerned with the problem of pre-filled syringes at all, because of their focus on destruction of the syringe after use.

Several U.S. Patents have addressed the problem of preventing removal of materials from pre-filled syringes.

For example, Sarnoff U.S. Pat. No. 3,126,004 discloses an improved syringe cartridge constructed to clearly disclose any removal and replacement of the piston, penetration thereof, or sliding of a needle between the piston and the glass wall of the cartridge to effect removal of cartridge contents. Sarnoff accomplishes this objective by placing a colored sealing wax material over the outer surface of the piston, which material would be disturbed if the piston were removed or which would be transferred into the cartridge if a needle were introduced between the piston and the cartridge.

While this method may indeed prevent tampering with the pre-filled syringe, this solution to the problem is a messy and complicated one which has not been put into practice in the almost twenty years since issue of this patent.

A second example in the art of attempts to prevent tampering with pre-filled syringes is Hobbs U.S. Pat. No. 3,666,113 in which (as in Sarnoff) the piston end is coated by a material. In contrast to Sarnoff, however, the material used in Hobbs is a thin layer of flexible plastic material which may optionally have a fluorescent dye imprint on it. Hobbs draws attention to the defects of the Sarnoff patent relating particularly to the brittleness of the sealing wax coating which could easily occur as a result of handling or shipping and thus give a false indication of tampering.

Hobbs seeks to solve this problem by employing a flexible plastic material adhering to the exterior surface of the cartridge barrel in the region of the open end so as to cover the piston. While this procedure may remove the difficulties attendant upon the Sarnoff device, it nevertheless is a relatively cumbersome apparatus to use and involves the necessary step of dipping the syringe end into the molten plastic material, which is seen to be a clear disadvantage.

In contrast to these prior art methods for preventing tampering with pre-filled syringes, the subject syringe is simple to construct and use but yet readily prevents surreptitious use and refilling of the syringe.

SUMMARY OF THE INVENTION

The present invention provides a disposable, nonreusable, pre-filled syringe which comprises:

(a) a barrel having a first open end having a restricted opening and a second end adapted to receive a hypodermic needle;

(b) a piston assembly within said barrel comprising a piston and plunger rod attached to the piston and extending out through the restricted opening of the first open end of the barrel, said plunger rod having a plurality of short, stiff, flexible spikes attached thereto at an oblique angle away from the piston; and (c) a fluid to be injected contained within said barrel between said piston and said second end of the barrel, whereby a push on the plunger rod will inject the fluid through the hypodermic needle since the oblique-angled spikes will contract to pass through the restricted opening, while a pull on the plunger rod will be resisted by the oblique-angled spikes, thus preventing aspiration of fluid into the barrel.

The individual parts and components of the subject syringe are all known in the art. The barrel may be of glass or any of the knon plastic materials. The piston may be of rubber or the like. Of course, the components should be chosen to be compatible with the fluid to be injected.

The plunger rod and the spikes are conveniently of a plastic material such as polyproplyene or the like. The spikes must be sufficiently flexible to pass through the restricted opening, while at the same time sufficiently stiff to open into their original position once inside the barrel and thus prevent withdrawal of the piston assembly.

Injectable fluids for which the subject syringe is especially suited include all injectable controlled substances such as morphine and morphinomimetics (e.g., dilantin, oxycodone, etc.), fentanyl, diazepam (Valium), and the like.

The subject invention thus provides a simple yet very effective means for determining whether tampering has occurred with a pre-filled syringe and for preventing the introduction of foreign materials into the syringe.

BRIEF DESCRIPTION OF THE DRAWINGS

FIG. 1 shows a plane view of the subject syringe loaded with injectable solution ready for use;

FIG. 2 shows a perspective view of the same syringe; and

FIG. 3 shows a plane view of the syringe after injection.

In FIGS. 1 and 2 is shown syringe 10 having barrel 11 with restricted opening 12, plunger rod 13 with spikes 14, and piston 15.

The use of the subject syringe is demonstrated in FIG. 3, in which force exerted on the end of plunger rod 13 has expelled the injectable solution through needle 16.

During the injection process, spikes 14 are slightly compressed to pass through restricted opening 12 and then expand to their original position once they are within the barrel. Thus, as shown in FIG. 3, withdrawal of the plunger assembly to aspire a foreign substance into the syringe is not possible because the spikes will not pass backwards through the restricted opening.

As illustrated by the figures, the subject invention solves in a simple fashion difficulties which have heretofore rendered the provision of such a device difficult if not impossible.

What is claimed is:

1. A disposable, non-reusable, pre-filled syringe comprising:
   (a) a barrel having a first open end having a restricted opening and a second end adapted to receive a hypodermic needle;
   (b) a piston assembly within said barrel comprising a piston and plunger rod attached to the piston and extending out through the restricted opening of the first open end of the barrel, said plunger rod having a plurality of short, stiff, flexible spikes attached thereto at an oblique angle away from the piston; and
   (c) a fluid to be injected contained within said barrel between said piston and said second end of the barrel,
   whereby a push on the plunger rod will inject the fluid through the hypodermic needle since the oblique-angled spikes will contract to pass through the restricted opening, while a pull on the plunger rod will be resisted by the oblique-angled spikes, thus preventing aspiration of fluid into the barrel.

2. The syringe of claim 1 which further comprises a hypodermic needle attached to the second end of the barrel.

3. The syringe of claim 1 wherein the fluid to be injected is a pharmaceutically acceptable injectable formulation containing fentanyl or morphine.

* * * * *